US005439881A

United States Patent [19]

Narva et al.

[11] Patent Number: 5,439,881

[45] **Date of Patent: * Aug. 8, 1995**

[54] **GENE ENCODING NEMATODE-ACTIVE TOXIN PS63B CLONED FROM *BACILLUS THURINGIENSIS* ISOLATE**

[75] Inventors: Kenneth E. Narva, San Diego; George E. Schwab, La Jolla; Jewel M. Payne, San Diego, all of Calif.

[73] Assignee: Mycogen Corporation, San Diego, Calif.

[*] Notice: The portion of the term of this patent subsequent to Aug. 14, 2007 has been disclaimed.

[21] Appl. No.: 49,783

[22] Filed: Apr. 19, 1993

Related U.S. Application Data

[60] Division of Ser. No. 693,018, May 3, 1991, abandoned, which is a continuation-in-part of Ser. No. 565,544, Jun. 29, 1990, abandoned, which is a continuation-in-part of Ser. No. 84,653, Aug. 12, 1987, Pat. No. 4,948,734.

[51] Int. Cl.$^6$ .................... A01N 63/02; C12N 15/32

[52] U.S. Cl. .................................... 514/2; 536/23.71; 424/93.461

[58] Field of Search .................... 536/23.71; 530/350; 424/936; 514/2

[56] References Cited

PUBLICATIONS

Coles, G. C., (1986) "Anthelmintic Resistance in Sheep" Veterinary Clinics of North America, Food Animal Practice 2(2):423–428.

Ciordia, H., and W. E. Bizzell (1961) "A Preliminary Report on the Effects of *Bacillus thuringiensis* var. *thuringiensis* Berliner on the Development of the Free-Living Stages of Some Cattle Nematodes" Jornal of Parasitology 47:41 *abstract*.

Bottjer, Kurt P., Leon W. Bone, and Sarjeet S. Gill (1985) "Nematoda: Susceptibility of the Egg to *Bacillus thuringiensis* Toxins" Experimental Parasitology 60:239–244.

Ignoffo, C. M., and V. H. Dropkin (1977) "Deleterious Effects of the Thermostable Toxin of *Bacillus thuringiensis* on Species of Soil-Inhabiting, Myceliophagus, and Plant-Parasitic Nematodes" Journal of the Kansas Entomological Society 50(3):394–398.

Prichard, R. K., C. A. Hall, J. D. Kelly, I. C. A. Martin, and A. D. Donald (1980) "The Problem of Anthelmintic Resistance in Nematodes" Australian Veterinary Journal 56:239–251.

*Primary Examiner*—Robert A. Wax
*Assistant Examiner*—Keith D. Hendricks
*Attorney, Agent, or Firm*—Saliwanchik & Saliwanchik

[57] ABSTRACT

This invention concerns genes or gene fragments which have been cloned from novel *Bacillus thuringiensis* isolates which have nematicidal activity. These genes or gene fragments can be used to transform suitable hosts for controlling nematodes.

2 Claims, No Drawings

GENE ENCODING NEMATODE-ACTIVE TOXIN PS63B CLONED FROM *BACILLUS THURINGIENSIS* ISOLATE

CROSS-REFERENCE TO A RELATED APPLICATION

This is a division of co-pending application Ser. No. 07/693,018, filed May 3, 1991, now abandoned, which is a continuation-in-part of co-pending application Ser. No. 07/565,544, filed on Aug. 10, 1990, now abandoned, which is a continuation-in-part of application Ser. No. 084,653, filed on Aug. 12, 1987, now U.S. Pat. No. 4,948,734.

BACKGROUND OF THE INVENTION

Regular use of chemicals to control unwanted organisms can select for drug resistant strains. This has occurred in many species of economically important insects and has also occurred in nematodes of sheep, goats, and horses. The development of drug resistance necessitates a continuing search for new control agents having different modes of action.

In recent times, the accepted methodology for control of nematodes has centered around the drug benzimidazole and its congeners. The use of these drugs on a wide scale has led to many instances of resistance among nematode populations (Prichard, R. K. et al. "The problem of anthelmintic resistance in nematodes," Austr. Vet. J. 56:239–251; Coles, G. C. [1986] "Anthelmintic resistance in sheep," In *Veterinary Clinics of North America: Food Animal Practice,* Vol 2:423–432 [Herd, R. P., eds.] W. B. Saunders, N.Y.). There are more than 100,000 described species of nematodes.

The bacterium *Bacillus thuringiensis* (B.t.) produces a δ-endotoxin polypeptide that has been shown to have activity against a rapidly growing number of insect species. The earlier observations of toxicity only against lepidopteran insects have been expanded with descriptions of B.t. isolates with toxicity to dipteran and coleopteran insects. These toxins are deposited as crystalline inclusions within the organism. Many strains of B.t. produce crystalline inclusions with no demonstrated toxicity to any insect tested.

A small number of research articles have been published about the effects of delta endotoxins from *B. thuringiensis* species on the viability of nematode eggs. Bottjer, Bone and Gill (Experimental Parasitology 60:239–244, 1985) have reported that *B. t. kurstaki* and *B. t. israelensis* were toxic in vitro to eggs of the nematode *Trichostrongylus colubriformis.* In addition, 28 other *B.t.* strains were tested with widely variable toxicities. The most potent had $LD_{50}$ values in the nanogram range. Ignoffo and Dropkin (Ignoffo, C. M. and Dropkin, V. H. [1977] J. Kans. Entomol. Soc. 50:394–398) have reported that the thermostable toxin from *Bacillus thuringiensis* (beta exotoxin) was active against a free-living nematode, *Panagrellus redivivus* (Goodey); a plant-parasitic nematode, *Meloidogyne incognita* (Chitwood); and a fungus-feeding nematode, *Aphelenchus avena* (Bastien). Beta exotoxin is a generalized cytotoxic agent with little or no specificity. Also, H. Ciordia and W. E. Bizzell (Jour. of Parasitology 47:41 [abstract] 1961) gave a preliminary report on the effects of *B. thuringiensis* on some cattle nematodes.

At the present time there is a need to have more effective means to control the many nematodes that cause considerable damage to susceptible hosts. Advantageously, such effective means would employ biological agents. In parent pending application Ser. No. 084,653, there are disclosed novel isolates of *Bacillus thuringiensis* having activity against nematodes. We have now isolated, unexpectedly and advantageously, genes encoding novel nematicidal δ-endotoxins from the B.t. isolates PS33F2, PS63B, PS52A1, and PS69D1. Prior to successfully completing this invention, we could not predict with any reasonable degree of certainty that we could isolate a gene(s) encoding a nematicidal toxin because of the complexity of the microbial genome.

BRIEF SUMMARY OF THE INVENTION

The subject invention concerns genes or gene fragments cloned from novel *Bacillus thuringiensis* isolates designated B.t. PS33F2, PS63B, PS52A1, and PS69D1. The genes or gene fragments of the invention encode *Bacillus thuringiensis* δ-endotoxins which have nematicidal activity. The genes or gene fragments can be transferred to suitable hosts via a recombinant DNA vector.

BRIEF DESCRIPTION OF THE SEQUENCES

Sequence ID 1 is the nucleotide sequence of a gene from PS33F2.

Sequence ID 2 is the amino acid sequence of the protein expressed by the gene from PS33F2.

Sequence ID 3 is the nucleotide sequence of a gene from PS52A1.

Sequence ID 4 is the amino acid sequence of the protein expressed by the gene from PS52A1.

Sequence ID 5 is the nucleotide sequence of a gene from PS69D1.

Sequence ID 6 is the amino acid sequence of the protein expressed by the gene from PS69D1.

SEQ ID NO. 7 is the N-terminal amino acid sequence for PS33F2.

SEQ ID. NO. 8 is the N-terminal amino acid sequence for PS52A1.

SEQ ID. NO. 9 is the N-terminal amino acid sequence for PS63B.

SEQ ID. NO. 10 is the N-terminal amino acid sequence for PS69D1.

SEQ ID. NO. 11 is the N-terminal amino acid sequence for PS63B(2).

SEQ ID. NO. 12 is a probe for 33F2A.

SEQ ID. NO. 13 is a probe for 33F2B.

SEQ ID. NO. 14 is a reverse primer used for closing the PS 33F 2toxin gene.

SEQ ID. NO. 15 is an oligonucloetide probe designated 52A1-C.

SEQ ID. NO. 16 is an oligonucleotide probe designed 69D1-D.

SEQ ID. NO. 17 is a forward primer designated 63B-A.

SEQ ID. NO. 18 is a reverse primer designated 63B-INT.

DETAILED DISCLOSURE OF THE INVENTION

The novel toxin genes or gene fragments of the subject invention were obtained from nematode-active *B. thuringiensis* (B.t.) isolates designated PS33F2, PS63B, PS52A1, and PS69D1. Subcultures of the *E. coli* host harboring the toxin genes of the invention were deposited in the permanent collection of the Northern Research Laboratory, U.S. Department of Agriculture, Peoria, Ill., USA. The accession numbers are as follows:

| Culture | Repository No. | Deposit Date |
|---|---|---|
| *B.t.* isolate PS33F2 | NRRL B-18244 | July 28, 1987 |
| *B.t.* isolate PS63B | NRRL B-18246 | July 28, 1987 |
| *B.t.* isolate PS52A1 | NRRL B-18245 | July 28, 1987 |
| *B.t.* isolate PS69D1 | NRRL B-18247 | July 28, 1987 |
| *E. coli* NM522(pMYC 2316) | NRRL B-18785 | March 15, 1991 |
| *E. coli* NM522(pMYC 2321) | NRRL B-18770 | February 14, 1991 |
| *E. coli* NM522(pMYC 2317) | NRRL B-18816 | April 24, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The novel B.t. genes or gene fragments of the invention encode toxins which show activity against tested nematodes. The group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, Caenorhabditis* and *Parascaris.* Certain of these, such as *Nematodirus, Cooperia,* and *Oesophagostomum,* attack primarily the intestinal tract, while others, such as *Dictyocaulus* are found in the lungs. Still other parasites may be located in other tissues and organs of the body.

The toxins encoded by the novel B.t. genes of the invention are useful as nematocides for the control of soil nematodes and plant parasites selected from the genera *Bursaphalenchus, Criconemella, Ditylenchus, Globodera, Helicotylenchus, Heterodera, Melodoigyne, Pratylenchus, Radolpholus, Rotelynchus,* or *Tylenchus.*

Alternatively, because some plant parasitic nematodes are obligate parasites, genes coding for nematocidal B.t. toxins can be engineered into plant cells to yield nematode-resistant plants. The methodology for engineering plant cells is well established (cf. Nester, E. W., Gordon, M. P., Amasino, R. M. and Yanofsky, M. F., Ann. Rev. Plant Physiol. 35:387–399, 1984).

The B.t. toxins of the invention can be administered orally in a unit dosage form such as a capsule, bolus or tablet, or as a liquid drench when used as an anthelmintic in mammals, and in the soil to control plant nematodes. The drench is normally a solution, suspension or dispersion of the active ingredient, usually in water, together with a suspending agent such as bentonitc and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight, the capsules and boluses comprise the active ingredient admixed with a carrier vehicle such as starch, talc, magnesium stearate, or dicalcium phosphate.

Where it is desired to administer the toxin compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent, depending upon the factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or, optionally, fed separately. Alternatively, the antiparasitic compounds may be administered to animals parenterally, for example, by intraruminal, intramuscular, intratracheal, or subcutaneous injection, in which event the active ingredient is dissolved or dispersed in a liquid carrier vehicle. For parenteral administration, the active material is suitably admixed with an acceptable vehicle, preferably of the vegetable oil variety, such as peanut oil, cotton seed off and the like. Other parenteral vehicles, such as organic preparations using solketal, glycerol, formal and aqueous parenteral formulations, are also used. The active compound or compounds are dissolved or suspended in the parenteral formulation for administration; such formulations generally contain from 0.005 to 5% by weight of the active compound.

When the toxins are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like.

The toxin genes or gene fragments of the subject invention can be introduced into a wide variety of microbial hosts. Expression of the toxin gene results, directly or indirectly, in the intracellular production and maintenance of the nematicide. With suitable hosts, e.g., Pseudomonas, the microbes can be applied to the situs of nematodes where they will proliferate and be ingested by the nematodes. The result is a control of the nematodes. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene or gene fragment is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the nematicide from environmental degradation and inactivation.

A large number of microorganisms are known to inhabit the phylloplane (the surface of the plant leaves) and/or the riosphere (the soft surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc,* and *Alcaligenes;* fungi, particularly yeast, e.g., genera *Saccharomyces, Cryptococcus, Kluyveromyces, Sporobolomyces, Rhodotorula,* and *Aureobasidium.* Of particular interest are such phytosphere bacterial species as *Pseudomonas syringae. Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus, and Azotobacter vinlandii*; and phytosphere yeast species such as *Rhodotorula rubra, R. glutinis, R. marina, R. aurantiaca, Cryptococcus albidus, C. diffiuens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are known and available for introducing the B.t. genes or gene fragments expressing the toxin into the microorganism host under conditions which allow for stable maintenance and expression of the gene. The transformants can be isolated in accordance with conventional ways, usually employing a selection technique, which allows for selection of the desired organism as against unmodified organisms or transferring organisms, when present. The transformants then can be tested for nematicidal activity.

Suitable host cells, where the nematicide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and positive, include Enterobacteriaceae, such as *Escherichia, Erwinia, Shigella, Salmonella,* and *Proteus; Bacillaceae; Rhizobiceae,* such as *Rhizobium; Spirillaceae,* such as photobacterium, *Zymomonas, Serratia, Aeromonas, Vibrio, Desulfovibrio, Spirillum; Lactobacillaceae; Pseudomonadaceae,* such as *Pseudomonas* and *Acetobacter; Azotobacteraceae* and *Nitrobacteraceae.* Among eukaryotes are fungi, such as Phycomycetes and Ascomycetes, which includes yeast, such as *Saccharomyces* and *Schizosaccharomyces;* and Basidiomycetes yeast, such as *Rhodotorula, Aureobasidium, Sporobolomyces,* and the like.

Characteristics of particular interest in selecting a host cell for purposes of production include ease of introducing the B.t. gene or gene fragment into the host, availability of expression systems, efficiency of expression, stability of the nematicide in the host, and the presence of auxiliary genetic capabilities. Characteristics of interest for use as a nematicide microcapsule include protective qualities for the nematicide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula* sp., *Aureobasidium* sp., *Saccharomyces* sp., and *Sporobolomyces* sp.; phylloplane organisms such as *Pseudomonas* sp., *Erwinia* sp. and *Flavobacterium* sp.; or such other organisms as *Escherichia, Lactobacillus* sp., *Bacillus* sp., and the like. Specific organisms include *Pseudomonas aeruginosa, Pseudomonas fluorescens, Saccharomyces cerevisiae, Bacillus thuringiensis, Escherichia coli, Bacillus subtilis*, and the like.

The cell will usually be intact and be substantially in the proliferative form when treated, rather than in a spore form, although in some instances spores may be employed.

Treatment of the microbial cell, e.g., a microbe containing the B.t. toxin gene or gene fragment, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. nematicidal gene or gene fragment may be grown in any convenient nutrient medium, where the DNA construct provides a selective advantage, providing for a selective medium so that substantially all or all of the cells retain the B.t. gene or gene fragment. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The nematicide concentration will vary widely depending upon the nature of the particular formulation, particularly whether it is a concentrate or to be used directly. The nematicide will be present in at least 1% by weight and may be 100% by weight. The dry formulations will have from about 1–95% by weight of the nematicide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the nematodes, e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

Example 1—Culturing B.t. Isolates of the Invention

A subculture of a B.t. isolate can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salts Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

Example 2—Purification of Protein and Amino Acid Sequencing

The B.t. isolates PS33F2, PS63B, PS52A1, and PS69D1 were cultured as described in Example 1. The parasporal inclusion bodies were partially purified by sodium bromide (28–38%) isopycnic gradient centrifugation (Pfannenstiel, M. A., E. J. Ross, V. C. Kramer, and K. W. Nickerson [1984] FEMS Microbiol. Lett. 21:39). The proteins toxic for the nematode *Caenorhabditis elegans* were bound to PVDF membranes (Millipore, Bedford, MA) by western blotting techniques (Towbin, H., T. Staehlelin, and K. Gordon [1979] Proc. Natl. Atari. Sci. USA 76:4350) and the N-terminal amino acid sequences were determined by the standard Edman reaction with an automated gas-phase sequenator (Hunkapiller, M. W., R. M. Hewick, W. L. Dreyer, and L. E. Hood[1983] Meth. Enzymol. 91:399). The sequences obtained were:

PS33F2ATLNEVYPVN
PS52A1 MIIDSKTTLPRHSLINT
PS63B QLQAQPLIPYNVLA
PS69D1 MILGNGKTLPKHIRLAHIFATQNS

In addition, internal amino acid sequence data were derived for PS63B. The toxin protein was partially digested with Staphylococcus aureus V8 protease (Sigma Chem. Co., St. Louis, MO) essentially as described (Cleveland, D. W., S. G. Fischer, M. W. Kirsclmer, and U. K. Laemrnli [1977] J. Biol. Chem. 252:1102). The digested material was blotted onto PVDF membrane and a ca. 28 kDa limit peptide was selected for N-terminal sequencing as described above. The sequence obtained was:

63B(2) VQRILDEKLSFQLIK

From these sequence data oligonucleotide probes were designed by utilizing a codon frequency table assembled from available sequence data of other B.t. toxin genes. The probes were synthesized on an Applied Biosystems, Inc. DNA synthesis machine.

Protein purification and subsequent amino acid analysis of the N-terminal peptides listed above has led to the deduction of several oligonucleotide probes for the isolation of toxin genes from nematicidal B.t. isolates. RFLP analysis of restricted total cellular DNA using radiolabeled oligonucleotide probes has elucidated different genes or gene fragments.

Example 3—Cloning of a Novel Toxin Gene From B.t. PS33F2 and Transformation into Escherichia coli Total cellular DNA was prepared from B.t. PS33F2 cells grown to an optical density, at 600 nm, of 1.0. Cells were pelleted by centrifugation and resuspended in protoplast buffer (20 mg/ml lysozyme in 0.3M sucrose, 25 mM Tris-Cl [pH 8.0], 25 mM EDTA). After incubation at 37° C. for 1 h, protoplasts were lysed by the addition of nine volumes of a solution of 0.1M NaCl, 0.1% SDS, 0.1 M Tris-C1 followed by two cycles of freezing and thawing. The cleared lysate was extracted twice with phenol:chloroform (1:1). Nucleic acids were precipitated with two volumes of ethanol and pelleted by centrifugation. The pellet was resuspended in 10mM Tris-Cl, 1 mM EDTA (TE) and RNase was added to a final concentration of 50 μg/ml. After incubation at 37° C. for 1 h, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE.

Plasmid DNA was extracted from protoplasts prepared as described above. Protoplasts were lysed by the addition of nine volumns of a solution of 10 mM Tris-Cl, 1 mM EDTA, 0.085 N NaOH, 0.1% SDS, pH=8.0. SDS was added to 1% final concentration to complete lysis. One-half volume of 3M KOAc was then added and the cellular material was precipitated overnight at 4° C. After centrifugation, the DNA was precipitated with ethanol and plasmids were purified by isopycnic centrifugation on cesium chloride-ethldium bromide gradients.

Restriction Fragment Length Polymorphism (RFLP) analyses were performed by standard hybridization of Southern blots of PS33F2 plasmid and total cellular DNA with 32P-labelled oligonucleotide probes designed to the N-terminal amino acid sequence disclosed in Example 2.

Probe 33F2A: 5'GCA/F ACA/T TYA AAT GAA GTA/T TAT 3'

Probe 33F2B: 5'AAT GAA GTA/T TAT CCA/T GTA/T AAT 3'

Hybridizing bands included an approximately 5.85 kbp EcoRI fragment. Probe 33F2A and a reverse PCR primer were used to amplify a DNA fragment of approximately 1.8 kbp for use as a hybridization probe for cloning the PS33F2 toxin gene. The sequence of the reverse primer was:

5'GCAAGCGGCCGCTTATGGAATAAATT-CAATT G A/G TC T/A A 3'

A gene library was constructed from PS33F2 plasmid DNA digested with EcoRI. Restriction digests were fractionated by agarose gel electrophoresis. DNA fragments 4.3–6.6 kbp were excised from the gel, electroeluted from the gel slice, and recovered by ethanol precipitation after purification on an Elutip-D ion exchange column (Schleicher and Schuel, Keene NH). The EcoRI inserts were ligated into EcoRI-digested pHTBlueII (an E. coli./B. thuringiensis shuttle vector comprised of pBluescript S/K [Stratagene] and the replication origin from a resident B.t. plasmid [D. Lereclus et al. 1989. FEMS Microbial. Lett. 60:211–218]). The ligation mixture was transformed into frozen, competent NM522 cells (ATCC 47000). Transformants were plated on LB agar containing ampicillin, isopropyl-(Beta)-D-thiogalactoside (IPTG), and 5-bromo-4-chloro-3-indolyl-(Beta)-D-galactoside (XGAL). Colonies were screened by hybridization with the radiolabeled PCR amplified probe described above. Plasmids were purified from putative toxin gene clones by alkaline lysis and analyzed by agarose gel electrophoresis of restriction digests. The desired plasmid construct, pMYC2316, contains an approximately 5.85 kbp EcoRI insert; the toxin gene residing on this DNA fragment (33F2a) is novel compared to the DNA sequences of other toxin genes encoding nematicidal proteins.

Plasmid pMYC2316 was introduced into the acrystallfferous (Cry-) B.t. host, HD-1 CryB (A. Aronson, Purdue University, West Lafayette, IN) by electroporation. Expression of an approximately 120–140 kDa crystal protein was verified by SDS-PAGE analysis. Crystals were purified on NaBr gradients (M. A. Pfannenstiel et al. 1984. FEMS Microbiol. Lett. 21:39) for determination of toxicity of the cloned gene product to Pratylenchus spp.

Example 4—Activity of the B.t. Gene Product PS33F2 Against the Plant Nematode Pratylenchus spp.

Pratylenchus spp. was reared aseptically on excised corn roots in Gamburg's B5 medium (GIBCO ® Laboratories, Grand Island, N.Y.) Bioassays were done in 24 well assay plates (Corning #25820) using L 3–4 larvae as described by Tsai and van Gundy (*J. Nematol.* 22(3):327–332). Approximately 20 nematodes were placed in each well. A total of 80–160 nematodes were used in each treatment. Samples of protein were suspended in an aqueous solution using a hand-held Dounce homogenizer.

Mortality was assessed visually 3 days after treatment. Larvae that were nearly straight and not moving were considered moribund. Representative results are as follows:

| PS33F2a (ppm) | % Moribund |
|---|---|
| 0 | 12 |
| 75 | 78 |

Species of *Pratylenchus*, for example *P. scribneri*, are known pathogens of many economically important crops including corn, peanuts, soybean, alfalfa, beans, tomato, and citrus. These "root lesion" nematodes are the second most economically damaging genus of plant parasitic nematodes (after *Meloidogyne*—the "root knot" nematode), and typify the migratory endoparasites.

Example 5—Molecular Cloning of Gene Encoding a Novel Toxin From *Bacillus thuringiensis* strain PS52A1

Total cellular DNA was prepared from Bacillus thuringiensis PS52A1 (B.t. PS52A1) as disclosed in Example 3.

RFLP analyses were performed by standard hybridization of Southern blots of PS52A1 DNA with a $^{32}P$-labeled oligonucleotide probe designed from the N-terminal amino acid sequence disclosed in Example 2. The sequence of this probe is:

5'ATG ATY ATT GAT TCT AAA ACA ACA TTA CCA AGA CAT TCA/T TYA ATA/T AAT ACA/T ATA/T AA 3'

This probe was designated 52A1-C. Hybridizing bands included an approximately 3.6 kbp Hind-III fragment and an approximately 8.6 kbp EcoRV fragment. A gene library was constructed from PS52A1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BamHI-digested LambdaGem-11 (Promega). Recombinant phage were packaged and plated on *E. coli* KW25 1 cells (Promega). Plaques were screened by hybridization with the radiolabeled 52A1-C oligonucleotide probe disclosed above. Hybridizing phage were plaque-purified and used to infect liquid cultures of E. coli KW25 1 cells for isolation of phage DNA by standard procedures (Maniatis et al.). For subcloning, preparative amounts of DNA were digested with EcoRI and SalI, and electrophoresed on an agarose gel. The approximately 3.1 kbp band containing the toxin gene was excised from the gel, electroeluted from the gel slice, and purified by ion exchange chromatography as above. The purified DNA insert was ligated into EcoRI+Sal-digested pHTBlueII (an E. coli/B. thuringiensis shuttle vector comprised of pBluescript S/K [Stratagene] and the replication origin from a resident B.t. plasmid [D. Lereclus et al. 1989. FEMS Microbiology Letters 60:211–218]). The ligation mix was used to transform frozen, competent E. coli NM522 cells (ATTCC 47000). Transformants were plated on LB agar containing ampicillin, isoprypyl-(Beta)-D-thiogalactoside (IPTG), and 5-Bromo-4-Chloro-3-indolyl-(Beta)-D-galactoside (XGAL). Plasmids were purified from putative recombinants by alkaline lysis (Maniatis et al.) and analyzed by electrophoresis of EcoRI and SalI digests on agarose gels. The desired plasmid construct, pMYC2321 contains a tom gene that is novel compared to the maps of other toxin genes encoding nematicidal proteins.

Plasmid pMYC2321 was introduced into an acrystalliferous (Cry-) B.t. host by electroporation. Expression of an approximately 55–60 kDa crystal protein was verified by SDS-PAGE analysis. NaBr-purified crystals were prepared as described in Example 3 for determination of toxicity of the cloned gene product to Pratylenchus spp.

Example 6—Activity of the B.t. PS52A1 Toxin Protein and Gene Product Against the Root Lesion Nematode, *Pratylenchus scribneri*

*Pratylenchus scribneri* was reared aseptically on excised corn roots in Gamburg's B5 medium (GIBCO ® Laboratories, Grand Island, N.Y.). Bioassays were done in 24 well assay plates (Corning #25820) using L 3–4 larvae as described by Tsai and Van Gundy (J. Nematol. 22(3):327–332). Approximately 20 nematodes were placed in each well. A total of 80–160 nematodes were used in each treatment. Samples of protein were suspended in aqueous solution using a hand-held homogenizer.

Mortality was assessed by prodding with a dull probe 7 days after treatment. Larvae that did not respond to prodding were considered moribund. Representative results are shown below.

| Rate (ppm) | Percent Moribund |
|---|---|
| 200 | 75 |

-continued

| Rate (ppm) | Percent Moribund |
|---|---|
| Control | 5 |

Example 7—Molecular Cloning of Gene Encoding a Novel Toxin From *Bacillus Thuringiensis* strain PS 69D1

Total cellular DNA was prepared from PS69D1 (B.t. PS69D1) as disclosed in Example 3. RFLP analyses were performed by standard hybridization of Southern blots of PS69D1 DNA with a 32P-labeled oligonucleotide probe designated as 69D1-D. The sequence of the 69D1-D probe was:

5'AAA CAT ATF AGA TTA GCA CAT ATF TTF GCA ACA CAA AA 3'Hybridizing bands included an approximately 2.0 kbp HindIII fragment.

A gene library was constructed from PS69D1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BamHI-digested LambdaGem-11 (Promega, Madison, WI). Recombinant phage were packaged and plated on E. coli KW25 1 cells (Promega, Madison, WI). Plaques were screened by hybridization with the radiolabeled 69D1-D oligonucleotide probe. Hybridizing phage were plaque-purified and used to infect liquid cultures of E. coli KW251 cells for isolation of phage DNA by standard procedures (Maniatis et al. [1982] Molecular Cloning: A Laboratory Manual, Cold Spring Harbor, N.Y.). For subcloning, preparative amounts of DNA were digested with HindIII and electrophoresed on an agarose gel. The approximately, 2.0 kbp band containing the toxin gene was excised from the gel, electroeluted from the gel slice, and purified by ion exchange chromatography as above. The purified DNA insert was ligated into HindIII-digested pHTBlueII (and E. coli/B.t. shuttle vector comprised of pBluescript S/K (Stratagene, San Diego, CA) and the replication origin from a resident B.t. plasmid (D. Lereclus et al [1989] FEMS Microbiol. Lett. 60:211–218)). The ligation mix was used to transform frozen, competent E. coli NM522 cells (ATCC 47000). Transformants were plated on LB agar contianging 5-Bromo-4-Chloro-3-indolyl-(Beta)-D-galactoside (XGAL). Plasmids were purified from putative recombinants by alkaline lysis (Maniatis et al., ibid.) and analyzed by electorphoresis of HindIII digests on agarose gels. The desired plasmid construct, pMYC2317, contains a toxin gene that is novel compared to the maps of other toxin genes encoding insecticidal proteins.

Example 8-Molecular Cloning of a Gene Encoding a Novel Toxin from *Bacillus thuringiensis* Strain PS63B Example 2 shows the aminoterminal and internal polypeptide sequences of the PS63B toxin protein as determined by standard Edman protein sequencing. From these sequences, two oligonucleotide primers were designed using a codon frequency table assembled from B.t. genes encoding δ-endotoxins. The sequence of the forward primer (63B-A) was complementary to the predicted DNA sequence at the 5'end of the gene:

63B-A-5'CAA T/CTA CAA GCA/T CAA CC 3'

The sequence of the reverse primer (63B-INT) was complementary to the inverse of the internal predicted DNA sequence:

63B-INT -5'TTC ATC TAA AAT TCT TTG AJTAC 3'

These primers were used in standard polymerase chain reactions (Cetus Corporation) to amplify an approximately 460 bp fragment of the 63B toxin gene for use as a DNA cloning probe. Standard Southern blots of total cellular DNA from PS63B were hybridized with the radiolabeled PCR probe. Hybridizing bands included an approximately 4.4 kbp XbaI fragment, an approximately 2.0 kbp HindlII fragment, and an approximately 6.4 kbp SpeI fragment.

Example 9—Insertion of Toxin Gene Into Plants

The novel gene coding for the novel nematicidal toxin, as disclosed herein, can be inserted into plant cells using the Ti plasmid from *Agrobacter tumefaciens*. Plant cells can then be caused to regenerate into plants (Zambryski, P., Joos, H., Gentello, C., Leeroans, J., Van Montague, M. and Schell, J [1983]Cell 32:1033–1043). A particularly useful vector in this regard is pEND4k (Klee, H. J., Yanofsky, M. F. and Nester, E. W. [1985] Biofrechnology 3:637–642). This plasmid can replicate both in plant cells and in bacteria and has multiple cloning sites for passenger genes. The toxin gene, for example, can be inserted into the BamHI site of pEND4K, propagated in E. coli, and transformed into appropriate plant cells.

Example 10—Cloning of Novel Hybrid B. thuringiensis Genes Into Baculoviruses

The novel hybrid gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennook, G.d., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156–2165). The gene coding for the novel protein toxin of the invention can be modified with BamHI linkers at appropriate regions both upstream and downstream from the coding region and inserted into the passenger site of one of the AcNPV vectors.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |

-continued

| | | | |
|---|---|---|---|
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a Y-end on the right. All DNA sequences given herein are those of the strand whose sequence correspond to the mRNA sequence, with thymine substituted for uracil. The letters stand for the purine or pyrimidine bases forming the deoxynucleotide sequence.

A=adenine
G=guanine
C=cytosine
T=thymine
X=T or C if Y is A or G
X=C if Y is C or T
Y=A, G, C or T if X is C
Y=A or G if X is T
W=C or A if Z is A or G
W—C if Z is C or T
Z=A, G, Cor T if W is C
Z=A or G if W is A
QR=TC if S is A, G, C or T; alternatively
QR=AG ff S is T or C
J=AorG
K=TorC
L=A, T, CorG
M=A, CorT The above shows that the novel amino acid sequence of the B.t. toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is substantially retained. Further, the invention also includes mutants of organisms hosting all or pan of a toxin encoding a gene of the invention. Such microbial mutants can be made by techniques well known to persons skilled in the art. For example, UV irradiation can be used to prepare mutants of host organisms. Likewise, such mutants may include asporogenous host cells which also can be prepared by procedures well known in the art.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual,* Cold Spring Harbor Laboratory, N.Y. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

SEQUENCE LISTING ( 1 ) GENERAL INFORMATION:

( i i i ) NUMBER OF SEQUENCES: 18

( 2 ) INFORMATION FOR SEQ ID NO:1 (PS33F2):

( i ) SEQUENCE CHARACTERISTICS:
( A ) LENGTH: 3771 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bacillus thuringiensis
( C ) INDIVIDUAL ISOLATE: 33f2

( v i i ) IMMEDIATE SOURCE:
( B ) CLONE: 33f2a ( i x ) FEATURE:
( A ) NAME/KEY: miscfeature
( B ) LOCATION: 4..24
( D ) OTHER INFORMATION: /function="oligonucleotide hybridization probe"
/ product="GCA/T ACA/T TTA AAT GAA GTA/T TAT"
/ standardname="probe a"
/ note="Probe A"

( i x ) FEATURE:
( A ) NAME/KEY: miscfeature
( B ) LOCATION: 13..33
( D ) OTHER INFORMATION: /function="oligonucleotide hybridization probe"
/ product="AAT GAA GTA/T TAT CCA/T GTA/T AAT"
/ standardname="Probe B"
/ label=probe-b
/ note="probe b"

( x i ) SEQUENCE DESCRIPTION: SEQ ID NO:1:

```
ATGGCTACAC TTAATGAAGT ATATCCTGTG AATTATAATG TATTATCTTC TGATGCTTTT    60
CAACAATTAG ATACAACAGG TTTTAAAAGT AAATATGATG AAATGATAAA AGCATTCGAA   120
AAAAAATGGA AAAAAGGGGC AAAAGGAAAA GACCTTTTAG ATGTTGCATG GACTTATATA   180
ACTACAGGAG AAATTGACCC TTTAAATGTA ATTAAAGGTG TTTTATCTGTATTAACTTTA    240
ATTCCTGAAG TTGGTACTGT GGCCTCTGCA GCAAGTACTA TTGTAAGTTT TATTTGGCCT   300
AAAATATTTG GAGATAAACC AAATGCAAAA AATATATTTG AAGAGCTCAA GCCTCAAATT   360
GAAGCATTAA TTCAACAAGA TATAACAAAC TATCAAGATG CAATTAATCA AAAAAAATTT   420
GACAGTCTTC AGAAAACAAT TAATCTATAT ACAGTAGCTA TAGATAACAA TGATTACGTA   480
ACAGCAAAAA CGCAACTCGA AAATCTAAAT TCTATACTTA CCTCAGATAT CTCCATATTT   540
ATTCCAGAAG GATATGAAAC TGGAGGTTTA CCTTATTATG CTATGGTTGC TAATGCTCAT   600
ATATTATTGT TAAGAGACGC TATAGTTAAT GCAGAGAAAT TAGGCTTTAG TGATAAAGAA   660
GTAGACACAC ATAAAAAATA TATCAAAATG ACAATACACA ATCATACTGA AGCAGTAATA   720
AAAGCATTCT TAAATGGACT TGACAAATTT AAGAGTTTAG ATGTAAATAG CTATAATAAA   780
AAAGCAAATT ATATTAAAGG TATGACAGAA ATGGTTCTTG ATCTAGTTGC TCTATGGCCA   840
ACTTTCGATC CAGATCATTA TCAAAAAGAA GTAGAAATTG AATTTACAAG AACTATTTCT   900
TCTCCAATTT ACCAACCTGT ACCTAAAAAC ATGCAAAATA CCTCTAGCTC TATTGTACCT   960
```

-continued

```
AGCGATCTAT TTCACTATCA AGGAGATCTT GTAAAATTAG AATTTTCTAC AAGAACGGAC 1020
AACGATGGTC TTGCAAAAAT TTTTACTGGT ATTCGAAACA CATTCTACAA ATCGCCTAAT 1080
ACTCATGAAA CATACCATGT AGATTTTAGT TATAATACCC AATCTAGTGG TAATATTTCA 1140
AGAGGCTCTT CAAATCCGAT TCCAATTGAT CTTAATAATC CCATTATTTC AACTTGTATT 1200
AGAAATTCAT TTTATAAGGC AATAGCGGGA TCTTCTGTTT TAGTTAATTT TAAAGATGGC 1260
ACTCAAGGGT ATGCATTTGC CCAAGCACCA ACAGGAGGTG CCTGGGACCA TTCTTTTATT 1320
GAATCTGATG GTGCCCCAGA AGGGCATAAA TTAAACTATA TTTATACTTC TCCAGGTGAT 1380
ACATTAAGAG ATTTCATCAA TGTATATACT CTTATAAGTA CTCCAACTAT AAATGAACTA 1440
TCAACAGAAA AAATCAAAGG CTTTCCTGCG GAAAAAGGAT ATATCAAAAA TCAAGGGATC 1500
ATGAAATATT ACGGTAAACC AGAATATATT AATGGAGCTC AACCAGTTAA TCTGGAAAAC 1560
CAGCAAACAT TAATATTCGA ATTTCATGCT TCAAAAACAG CTCAATATAC CATTCGTATA 1620
CGTTATGCCA GTACCCAAGG AACAAAAGGT TATTTTCGTT TAGATAATCA GGAACTGCAA 1680
ACGCTTAATA TACCTACTTC ACACAACGGT TATGTAACCG GTAATATTGG TGAAAATTAT 1740
GATTTATATA CAATAGGTTC ATATACAATT ACAGAAGGTA ACCATACTCT TCAAATCCAA 1800
CATAATGATA AAAATGGAAT GGTTTTAGAT CGTATTGAAT TTGTTCCTAA AGATTCACTT 1860
CAAGATTCAC CTCAAGATTC ACCTCCAGAA GTTCACGAAT CAACAATTAT TTTTGATAAA 1920
TCATCTCCAA CTATATGGTC TTCTAACAAA CACTCATATA GCCATATACA TTTAGAAGGA 1980
TCATATACAA GTCAGGGAAG TTATCCACAC AATTTATTAA TTAATTTATT TCATCCTACA 2040
GACCCTAACA GAAATCATAC TATTCATGTT AACAATGGTG ATATGAATGT TGATTATGGA 2100
AAAGATTCTG TAGCCGATGG GTTAAATTTT AATAAAATAA CTGCTACGAT ACCAAGTGAT 2160
GCTTGGTATA GCGGTACTAT TACTTCTATG CACTTATTTA ATGATAATAA TTTTAAAACA 2220
ATAACTCCTA AATTTGAACT TTCTAATGAA TTAGAAAACA TCACAACTCA AGTAAATGCT 2280
TTATTCGCAT CTAGTGCACA AGATACTCTC GCAAGTAATG TAAGTGATTA CTGGATTGAA 2340
CAGGTCGTTA TGAAAGTCGA TGCCTTATCA GATGAAGTAT TTGGAAAAGA GAAAAAAGCA 2400
TTACGTAAAT TGGTAAATCA AGCAAAACGT CTCAGTAAAA TACGAAATCT TCTCATAGGT 2460
GGTAATTTTG ACAATTTAGT CGCTTGGTAT ATGGGAAAAG ATGTAGTAAA AGAATCGGAT 2520
CATGAATTAT TTAAAAGTGA TCATGTCTTA CTACCTCCCC CAACATTCCATCCTTCTTAT 2580
ATTTTCCAAA AGGTGGAAGA ATCAAAACTA AAACCAAATA CACGTTATAC TATTTCTGGT 2640
TTTATCGCAC ATGGAGAAGA TGTAGAGCTT GTTGTCTCTC GTTATGGGCA AGAAATACAA 2700
AAAGTGATGC AAGTGCCATA TGAAGAAGCA CTTCCTCTTA CATCTGAATC TAATTCTAGT 2760
TGTTGTGTTC CAAATTTAAA TATAAATGAA ACACTAGCTG ATCCACATTT CTTTAGTTAT 2820
AGCATCGATG TTGGTTCTCT GGAAATGGAA GCGAATCCTG GTATTGAATT TGGTCTCCGT 2880
ATTGTCAAAC CAACAGGTAT GGCACGTGTA AGTAATTTAG AAATTCGAGA AGACCGTCCA 2940
TTAACAGCAA AAGAAATTCG TCAAGTACAA CGTGCAGCAA GAGATTGGAA ACAAAACTAT 3000
GAACAAGAAC GAACAGAGAT CACAGCTATA ATTCAACCTG TTCTTAATCA AATTAATGCG 3060
TTATACGAAA ATGAAGATTG GAATGGTTCT ATTCGTTCAA ATGTTTCCTA TCATGATCTA 3120
GAGCAAATTA TGCTTCCTAC TTTATTAAAA ACTGAGGAAA TAAATTGTAA TTATGATCAT 3180
CCAGCTTTTT TATTAAAAGT ATATCATTGG TTTATGACAG ATCGTATAGG AGAACATGGT 3240
ACTATTTTAG CACGTTTCCA AGAAGCATTA GATCGTGCAT ATACACAATT AGAAAGTCGT 3300
AATCTCCTGC ATAACGGTCA TTTTACAACT GATACAGCGA ATTGGACAAT AGAAGGAGAT 3360
GCCCATCATA CAATCTTAGA AGATGGTAGA CGTGTGTTAC GTTTACCAGA TTGGTCTTCT 3420
```

-continued

```
AATGCAACTC AAACAATTGA AATTGAAGAT TTTGACTTAG ATCAAGAATA CCAATTGCTC   3480

ATTCATGCAA AAGGAAAAGG TTCCATTACT TTACAACATG GAGAAGAAAA CGAATATGTG   3540

GAAACACATA CTCATCATAC AAATGATTTT ATAACATCCC AAAATATTCC TTTCACTTTT   3600

AAAGGAAATC AAATTGAAGT CCATATTACT TCAGAAGATG GAGAGTTTTT AATCGATCAC   3660

ATTACAGTAA TAGAAGTTTC TAAAACAGAC ACAAATACAA ATATTATTGA AAATTCACCA   3720

ATCAATACAA GTATGAATAG TAATGTAAGA GTAGATATAC CAAGAAGTCT C            3771
```

( 2 ) INFORMATION FOR SEQ ID NO:2 (PS33F2):

( i ) SEQUENCE CHARACTERISTICS:
( A ) LENGTH: 1257 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: Bacillus thuringiensis
( C ) INDIVIDUAL ISOLATE: PS33F2

( v i i ) IMMEDIATE SOURCE:
( B ) CLONE: PS33F2a ( i x ) FEATURE:
( A ) NAME/KEY: Protein
( B ) LOCATION: 1..1257

( x i ) SEQUENCE DESCRIPTION: SEQ ID NO:2:

```
Met Ala Thr Leu Asn Glu Val Tyr Pro Val Asn Tyr Asn Val Leu Ser
1               5                   10                  15

Ser Asp Ala Phe Gln Gln Leu Asp Thr Thr Gly Phe Lys Ser Lys Tyr
            20                  25                  30

Asp Glu Met Ile Lys Ala Phe Glu Lys Lys Trp Lys Lys Gly Ala Lys
        35                  40                  45

Gly Lys Asp Leu Leu Asp Val Ala Trp Thr Tyr Ile Thr Thr Gly Glu
    50                  55                  60

Ile Asp Pro Leu Asn Val Ile Lys Gly Val Leu Ser Val Leu Thr Leu
65                  70                  75                  80

Ile Pro Glu Val Gly Thr Val Ala Ser Ala Ala Ser Thr Ile Val Ser
                85                  90                  95

Phe Ile Trp Pro Lys Ile Phe Gly Asp Lys Pro Asn Ala Lys Asn Ile
            100                 105                 110

Phe Glu Glu Leu Lys Pro Gln Ile Glu Ala Leu Ile Gln Gln Asp Ile
        115                 120                 125

Thr Asn Tyr Gln Asp Ala Ile Asn Gln Lys Lys Phe Asp Ser Leu Gln
    130                 135                 140

Lys Thr Ile Asn Leu Tyr Thr Val Ala Ile Asp Asn Asn Asp Tyr Val
145                 150                 155                 160

Thr Ala Lys Thr Gln Leu Glu Asn Leu Asn Ser Ile Leu Thr Ser Asp
                165                 170                 175

Ile Ser Ile Phe Ile Pro Glu Gly Tyr Glu Thr Gly Gly Leu Pro Tyr
            180                 185                 190

Tyr Ala Met Val Ala Asn Ala His Ile Leu Leu Leu Arg Asp Ala Ile
        195                 200                 205

Val Asn Ala Glu Lys Leu Gly Phe Ser Asp Lys Glu Val Asp Thr His
    210                 215                 220
```

-continued

```
Lys Lys Tyr Ile Lys Met Thr Ile His Asn His Thr Glu Ala Val Ile
225                 230                 235                 240

Lys Ala Phe Leu Asn Gly Leu Asp Lys Phe Lys Ser Leu Asp Val Asn
                245                 250                 255

Ser Tyr Asn Lys Lys Ala Asn Tyr Ile Lys Gly Met Thr Glu Met Val
            260                 265                 270

Leu Asp Leu Val Ala Leu Trp Pro Thr Phe Asp Pro Asp His Tyr Gln
        275                 280                 285

Lys Glu Val Glu Ile Glu Phe Thr Arg Thr Ile Ser Ser Pro Ile Tyr
    290                 295                 300

Gln Pro Val Pro Lys Asn Met Gln Asn Thr Ser Ser Ser Ile Val Pro
305                 310                 315                 320

Ser Asp Leu Phe His Tyr Gln Gly Asp Leu Val Lys Leu Glu Phe Ser
                325                 330                 335

Thr Arg Thr Asp Asn Asp Gly Leu Ala Lys Ile Phe Thr Gly Ile Arg
            340                 345                 350

Asn Thr Phe Tyr Lys Ser Pro Asn Thr His Glu Thr Tyr His Val Asp
        355                 360                 365

Phe Ser Tyr Asn Thr Gln Ser Ser Gly Asn Ile Ser Arg Gly Ser Ser
    370                 375                 380

Asn Pro Ile Pro Ile Asp Leu Asn Asn Pro Ile Ile Ser Thr Cys Ile
385                 390                 395                 400

Arg Asn Ser Phe Tyr Lys Ala Ile Ala Gly Ser Ser Val Leu Val Asn
                405                 410                 415

Phe Lys Asp Gly Thr Gln Gly Tyr Ala Phe Ala Gln Ala Pro Thr Gly
            420                 425                 430

Gly Ala Trp Asp His Ser Phe Ile Glu Ser Asp Gly Ala Pro Glu Gly
        435                 440                 445

His Lys Leu Asn Tyr Ile Tyr Thr Ser Pro Gly Asp Thr Leu Arg Asp
    450                 455                 460

Phe Ile Asn Val Tyr Thr Leu Ile Ser Thr Pro Thr Ile Asn Glu Leu
465                 470                 475                 480

Ser Thr Glu Lys Ile Lys Gly Phe Pro Ala Glu Lys Gly Tyr Ile Lys
                485                 490                 495

Asn Gln Gly Ile Met Lys Tyr Tyr Gly Lys Pro Glu Tyr Ile Asn Gly
            500                 505                 510

Ala Gln Pro Val Asn Leu Glu Asn Gln Gln Thr Leu Ile Phe Glu Phe
        515                 520                 525

His Ala Ser Lys Thr Ala Gln Tyr Thr Ile Arg Ile Arg Tyr Ala Ser
    530                 535                 540

Thr Gln Gly Thr Lys Gly Tyr Phe Arg Leu Asp Asn Gln Glu Leu Gln
545                 550                 555                 560

Thr Leu Asn Ile Pro Thr Ser His Asn Gly Tyr Val Thr Gly Asn Ile
                565                 570                 575

Gly Glu Asn Tyr Asp Leu Tyr Thr Ile Gly Ser Tyr Thr Ile Thr Glu
            580                 585                 590

Gly Asn His Thr Leu Gln Ile Gln His Asn Asp Lys Asn Gly Met Val
        595                 600                 605

Leu Asp Arg Ile Glu Phe Val Pro Lys Asp Ser Leu Gln Asp Ser Pro
    610                 615                 620

Gln Asp Ser Pro Pro Glu Val His Glu Ser Thr Ile Ile Phe Asp Lys
625                 630                 635                 640

Ser Ser Pro Thr Ile Trp Ser Ser Asn Lys His Ser Tyr Ser His Ile
                645                 650                 655

His Leu Glu Gly Ser Tyr Thr Ser Gln Gly Ser Tyr Pro His Asn Leu
```

-continued 660 665 670

Leu Ile Asn Leu Phe His Pro Thr Asp Pro Asn Arg Asn His Thr Ile
675 680 685

His Val Asn Asn Gly Asp Met Asn Val Asp Tyr Gly Lys Asp Ser Val
690 695 700

Ala Asp Gly Leu Asn Phe Asn Lys Ile Thr Ala Thr Ile Pro Ser Asp
705 710 715 720

Ala Trp Tyr Ser Gly Thr Ile Thr Ser Met His Leu Phe Asn Asp Asn
725 730 735

Asn Phe Lys Thr Ile Thr Pro Lys Phe Glu Leu Ser Asn Glu Leu Glu
740 745 750

Asn Ile Thr Thr Gln Val Asn Ala Leu Phe Ala Ser Ser Ala Gln Asp
755 760 765

Thr Leu Ala Ser Asn Val Ser Asp Tyr Trp Ile Glu Gln Val Val Met
770 775 780

Lys Val Asp Ala Leu Ser Asp Glu Val Phe Gly Lys Glu Lys Lys Ala
785 790 795 800

Leu Arg Lys Leu Val Asn Gln Ala Lys Arg Leu Ser Lys Ile Arg Asn
805 810 815

Leu Leu Ile Gly Gly Asn Phe Asp Asn Leu Val Ala Trp Tyr Met Gly
820 825 830

Lys Asp Val Val Lys Glu Ser Asp His Glu Leu Phe Lys Ser Asp His
835 840 845

Val Leu Leu Pro Pro Pro Thr Phe His Pro Ser Tyr Ile Phe Gln Lys
850 855 860

Val Glu Glu Ser Lys Leu Lys Pro Asn Thr Arg Tyr Thr Ile Ser Gly
865 870 875 880

Phe Ile Ala His Gly Glu Asp Val Glu Leu Val Val Ser Arg Tyr Gly
885 890 895

Gln Glu Ile Gln Lys Val Met Gln Val Pro Tyr Glu Glu Ala Leu Pro
900 905 910

Leu Thr Ser Glu Ser Asn Ser Ser Cys Cys Val Pro Asn Leu Asn Ile
915 920 925

Asn Glu Thr Leu Ala Asp Pro His Phe Phe Ser Tyr Ser Ile Asp Val
930 935 940

Gly Ser Leu Glu Met Glu Ala Asn Pro Gly Ile Glu Phe Gly Leu Arg
945 950 955 960

Ile Val Lys Pro Thr Gly Met Ala Arg Val Ser Asn Leu Glu Ile Arg
965 970 975

Glu Asp Arg Pro Leu Thr Ala Lys Glu Ile Arg Gln Val Gln Arg Ala
980 985 990

Ala Arg Asp Trp Lys Gln Asn Tyr Glu Gln Glu Arg Thr Glu Ile Thr
995 1000 1005

Ala Ile Ile Gln Pro Val Leu Asn Gln Ile Asn Ala Leu Tyr Glu Asn
1010 1015 1020

Glu Asp Trp Asn Gly Ser Ile Arg Ser Asn Val Ser Tyr His Asp Leu
1025 1030 1035 1040

Glu Gln Ile Met Leu Pro Thr Leu Leu Lys Thr Glu Glu Ile Asn Cys
1045 1050 1055

Asn Tyr Asp His Pro Ala Phe Leu Leu Lys Val Tyr His Trp Phe Met
1060 1065 1070

Thr Asp Arg Ile Gly Glu His Gly Thr Ile Leu Ala Arg Phe Gln Glu
1075 1080 1085

Ala Leu Asp Arg Ala Tyr Thr Gln Leu Glu Ser Arg Asn Leu Leu His
1090 1095 1100

-continued

Asn Gly His Phe Thr Thr Asp Thr Ala Asn Trp Thr Ile Glu Gly Asp
1105 1110 1115 1120

Ala His His Thr Ile Leu Glu Asp Gly Arg Arg Val Leu Arg Leu Pro
1125 1130 1135

Asp Trp Ser Ser Asn Ala Thr Gln Thr Ile Glu Ile Glu Asp Phe Asp
1140 1145 1150

Leu Asp Gln Glu Tyr Gln Leu Leu Ile His Ala Lys Gly Lys Gly Ser
1155 1160 1165

Ile Thr Leu Gln His Gly Glu Glu Asn Glu Tyr Val Glu Thr His Thr
1170 1175 1180

His His Thr Asn Asp Phe Ile Thr Ser Gln Asn Ile Pro Phe Thr Phe
1185 1190 1195 1200

Lys Gly Asn Gln Ile Glu Val His Ile Thr Ser Glu Asp Gly Glu Phe
1205 1210 1215

Leu Ile Asp His Ile Thr Val Ile Glu Val Ser Lys Thr Asp Thr Asn
1220 1225 1230

Thr Asn Ile Ile Glu Asn Ser Pro Ile Asn Thr Ser Met Asn Ser Asn
1235 1240 1245

Val Arg Val Asp Ile Pro Arg Ser Leu
1250 1255

( 2 ) INFORMATION FOR SEQ ID NO:3 (PS52A1):

( i ) SEQUENCE CHARACTERISTICS:
( A ) LENGTH: 1425 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS
( C ) INDIVIDUAL ISOLATE: PS52A1

( v i i ) IMMEDIATE SOURCE:
( A ) LIBRARY: LAMBDAGEM(TM)-11 LIBRARY OF KENNETH NARVA
( B ) CLONE: PS52A1-A ( i x ) FEATURE:
( A ) NAME/KEY: matpeptide
( B ) LOCATION: 1..1425
( D ) OTHER INFORMATION: /product="OPEN READING FRAME OF MATURE PROTEIN"

( x i ) SEQUENCE DESCRIPTION: SEQ ID NO:3:

ATGATTATTG ATAGTAAAAC GACTTTACCT AGACATTCAC TTATTCATAC AATTAAATTA 60

AATTCTAATA AGAAATATGG TCCTGGTGAT ATGACTAATG GAAATCAATT TATTATTTCA 120

AAACAAGAAT GGGCTACGAT TGGAGCATAT ATTCAGACTG GATTAGGTTT ACCAGTAAAT 180

GAACAACAAT TAAGAACACA TGTTAATTTA AGTCAGGATA TATCAATACC TAGTGATTTT 240

TCTCAATTAT ATGATGTTTA TTGTTCTGAT AAAACTTCAG CAGAATGGTG GAATAAAAAT 300

TTATATCCTT TAATTATTAA ATCTGCTAAT GATATTGCTT CATATGGTTT TAAAGTTGCT 360

GGTGATCCTT CTATTAAGAA AGATGGATAT TTTAAAAAAT TGCAAGATGA ATTAGATAAT 420

ATTGTTGATA ATAATTCCGA TGATGATGCA ATAGCTAAAG CTATTAAAGA TTTTAAAGCG 480

CGATGTGGTA TTTTAATTAA AGAAGCTAAA CAATATGAAG AAGCTGCAAA AAATATTGTA 540

ACATCTTTAG ATCAATTTTT ACATGGTGAT CAGAAAAAAT TAGAAGGTGT TATCAATATT 600

-continued

```
CAAAAACGTT TAAAAGAAGT TCAAACAGCT CTTAATCAAG CCCATGGGGA AAGTAGTCCA   660

GCTCATAAAG AGTTATTAGA AAAAGTAAAA AATTTAAAAA CAACATTAGA AAGGACTATT   720

AAAGCTGAAC AAGATTTAGA GAAAAAAGTA GAATATAGTT TTCTATTAGG ACCATTGTTA   780

GGATTTGTTG TTTATGAAAT TCTTGAAAAT ACTGCTGTTC AGCATATAAA AAATCAAATT   840

GATGAGATAA AGAAACAATT AGATTCTGCT CAGCATGATT TGGATAGAGA TGTTAAAATT   900

ATAGGAATGT TAAATAGTAT TAATACAGAT ATTGATAATT TATATAGTCA AGGACAAGAA   960

GCAATTAAAG TTTTCCAAAA GTTACAAGGT ATTTGGGCTA CTATTGGAGC TCAAATAGAA  1020

AATCTTAGAA CAACGTCGTT ACAAGAAGTT CAAGATTCTG ATGATGCTGA TGAGATACAA  1080

ATTGAACTTG AGGACGCTTC TGATGCTTGG TTAGTTGTGG CTCAAGAAGC TCGTGATTTT  1140

ACACTAAATG CTTATTCAAC TAATAGTAGA CAAAATTTAC CGATTAATGT TATATCAGAT  1200

TCATGTAATT GTTCAACAAC AAATATGACA TCAAATCAAT ACAGTAATCC AACAACAAAT  1260

ATGACATCAA ATCAATATAT GATTTCACAT GAATATACAA GTTTACCAAA TAATTTTATG  1320

TTATCAAGAA ATAGTAATTT AGAATATAAA TGTCCTGAAA ATAATTTTAT GATATATTGG  1380

TATAATAATT CGGATTGGTA TAATAATTCG GATTGGTATA ATAAT                  1425
```

( 2 ) INFORMATION FOR SEQ ID NO:4 (PS52A1):

( i ) SEQUENCE CHARACTERISTICS:
( A ) LENGTH: 475 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( C ) INDIVIDUAL ISOLATE: PS52A1

( v i i ) IMMEDIATE SOURCE:
( A ) LIBRARY: LAMBDAGEM(TM)-11 LIBRARY OF KENNETH NARVA
( B ) CLONE: PS52A1-A ( i x ) FEATURE:
( A ) NAME/KEY: Protein
( B ) LOCATION: 1..475

( x i ) SEQUENCE DESCRIPTION: SEQ ID NO:4:

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
```

-continued 130 135 140

Asn Ser Asp Asp Asp Ala Ile Ala Lys Ala Ile Lys Asp Phe Lys Ala
145 150 155 160

Arg Cys Gly Ile Leu Ile Lys Glu Ala Lys Gln Tyr Glu Glu Ala Ala
165 170 175

Lys Asn Ile Val Thr Ser Leu Asp Gln Phe Leu His Gly Asp Gln Lys
180 185 190

Lys Leu Glu Gly Val Ile Asn Ile Gln Lys Arg Leu Lys Glu Val Gln
195 200 205

Thr Ala Leu Asn Gln Ala His Gly Glu Ser Ser Pro Ala His Lys Glu
210 215 220

Leu Leu Glu Lys Val Lys Asn Leu Lys Thr Thr Leu Glu Arg Thr Ile
225 230 235 240

Lys Ala Glu Gln Asp Leu Glu Lys Lys Val Glu Tyr Ser Phe Leu Leu
245 250 255

Gly Pro Leu Leu Gly Phe Val Val Tyr Glu Ile Leu Glu Asn Thr Ala
260 265 270

Val Gln His Ile Lys Asn Gln Ile Asp Glu Ile Lys Lys Gln Leu Asp
275 280 285

Ser Ala Gln His Asp Leu Asp Arg Asp Val Lys Ile Ile Gly Met Leu
290 295 300

Asn Ser Ile Asn Thr Asp Ile Asp Asn Leu Tyr Ser Gln Gly Gln Glu
305 310 315 320

Ala Ile Lys Val Phe Gln Lys Leu Gln Gly Ile Trp Ala Thr Ile Gly
325 330 335

Ala Gln Ile Glu Asn Leu Arg Thr Thr Ser Leu Gln Glu Val Gln Asp
340 345 350

Ser Asp Asp Ala Asp Glu Ile Gln Ile Glu Leu Glu Asp Ala Ser Asp
355 360 365

Ala Trp Leu Val Val Ala Gln Glu Ala Arg Asp Phe Thr Leu Asn Ala
370 375 380

Tyr Ser Thr Asn Ser Arg Gln Asn Leu Pro Ile Asn Val Ile Ser Asp
385 390 395 400

Ser Cys Asn Cys Ser Thr Thr Asn Met Thr Ser Asn Gln Tyr Ser Asn
405 410 415

Pro Thr Thr Asn Met Thr Ser Asn Gln Tyr Met Ile Ser His Glu Tyr
420 425 430

Thr Ser Leu Pro Asn Asn Phe Met Leu Ser Arg Asn Ser Asn Leu Glu
435 440 445

Tyr Lys Cys Pro Glu Asn Asn Phe Met Ile Tyr Trp Tyr Asn Asn Ser
450 455 460

Asp Trp Tyr Asn Asn Ser Asp Trp Tyr Asn Asn
465 470 475

( 2 ) INFORMATION FOR SEQ ID NO:5 (PS69D1):

( i ) SEQUENCE CHARACTERISTICS:
( A ) LENGTH: 1185 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: BACILLUS THURINGIENSIS

-continued ( C ) INDIVIDUAL ISOLATE: PS69D1

( v i i ) IMMEDIATE SOURCE:
( A ) LIBRARY: LAMBDAGEM(TM)-11 LIBRARY OF KENNETH NARVA
( B ) CLONE: PS69D1A ( i x ) FEATURE:
( A ) NAME/KEY: matpeptide
( B ) LOCATION: 1..1185

( x i ) SEQUENCE DESCRIPTION: SEQ ID NO:5:

```
ATGATTTTAG GGAATGGAAA GACTTTACCA AAGCATATAA GATTAGCTCA TATTTTTGCA   60
ACACAGAATT CTTCAGCTAA GAAAGACAAT CCTCTTGGAC CAGAGGGGAT GGTTACTAAA  120
GACGGTTTTA TAATCTCTAA GGAAGAATGG GCATTTGTGC AGGCCTATGT GACTACAGGC  180
ACTGGTTTAC CTATCAATGA CGATGAGATG CGTAGACATG TTGGGTTACC ATCACGCATT  240
CAAATTCCTG ATGATTTTAA TCAATTATAT AAGGTTTATA ATGAAGATAA ACATTTATGC  300
AGTTGGTGGA ATGGTTTCTT GTTTCCATTA GTTCTTAAAA CAGCTAATGA TATTTCCGCT  360
TACGGATTTA AATGTGCTGG AAAGGGTGCC ACTAAAGGAT ATTATGAGGT CATGCAAGAC  420
GATGTAGAAA ATATTTCAGA TAATGGTTAT GATAAAGTTG CACAAGAAAA AGCACATAAG  480
GATCTGCAGG CGCGTTGTAA AATCCTTATT AAGGAGGCTG ATCAATATAA AGCTGCAGCG  540
GATGATGTTT CAAAACATTT AAACACATTT CTTAAAGGCG GTCAAGATTC AGATGGCAAT  600
GATGTTATTG GCGTAGAGGC TGTTCAAGTA CAACTAGCAC AAGTAAAAGA TAATCTTGAT  660
GGCCTATATG GCGACAAAAG CCCAAGACAT GAAGAGTTAC TAAAGAAAGT AGACGACCTG  720
AAAAAAGAGT TGGAAGCTGC TATTAAAGCA GAGAATGAAT TAGAAAAGAA AGTGAAAATG  780
AGTTTTGCTT TAGGACCATT ACTTGGATTT GTTGTATATG AAATCTTAGA GCTAACTGCG  840
GTCAAAAGTA TACACAAGAA AGTTGAGGCA CTACAAGCCG AGCTTGACAC TGCTAATGAT  900
GAACTCGACA GAGATGTAAA AATCTTAGGA ATGATGAATA GCATTGACAC TGATATTGAC  960
AACATGTTAG AGCAAGGTGA GCAAGCTCTT GTTGTATTTA GAAAAATTGC AGGCATTTGG 1020
AGTGTTATAA GTCTTAATAT CGGCAATCTT CGAGAAACAT CTTTAAAAGA GATAGAAGAA 1080
GAAAATGATG ACGATGCACT GTATATTGAG CTTGGTGATG CCGCTGGTCA ATGGAAAGAG 1140
ATAGCCGAGG AGGCACAATC CTTTGTACTA AATGCTTATA CTCCT                 1185
```

( 2 ) INFORMATION FOR SEQ ID NO:6 (PS69D1):

( i ) SEQUENCE CHARACTERISTICS:
( A ) LENGTH: 395 amino acids
( B ) TYPE: amino acid
( C ) STRANDEDNESS: single
( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
( A ) ORGANISM: BACILLUS THURINGIENSIS
( C ) INDIVIDUAL ISOLATE: PS69D1

( v i i ) IMMEDIATE SOURCE:
( A ) LIBRARY: LAMBDAGEM(TM)-11 LIBRARY OF KENNETH NARVA
( B ) CLONE: PS69D1A ( i x ) FEATURE:
( A ) NAME/KEY: Protein
( B ) LOCATION: 1..395

( x i ) SEQUENCE DESCRIPTION: SEQ ID NO:6:

```
Met Ile Leu Gly Asn Gly Lys Thr Leu Pro Lys His Ile Arg Leu Ala
```

-continued

| 1 | | | | 5 | | | | | 10 | | | | | 15 | |
|---|---|---|---|---|---|---|---|---|---|---|---|---|---|---|---|
| His | Ile | Phe | Ala | Thr | Gln | Asn | Ser | Ser | Ala | Lys | Lys | Asp | Asn | Pro | Leu |
| | | | 20 | | | | | 25 | | | | | 30 | | |
| Gly | Pro | Glu | Gly | Met | Val | Thr | Lys | Asp | Gly | Phe | Ile | Ile | Ser | Lys | Glu |
| | | 35 | | | | | 40 | | | | | 45 | | | |
| Glu | Trp | Ala | Phe | Val | Gln | Ala | Tyr | Val | Thr | Thr | Gly | Thr | Gly | Leu | Pro |
| | 50 | | | | | 55 | | | | | 60 | | | | |
| Ile | Asn | Asp | Asp | Glu | Met | Arg | Arg | His | Val | Gly | Leu | Pro | Ser | Arg | Ile |
| 65 | | | | | 70 | | | | | 75 | | | | | 80 |
| Gln | Ile | Pro | Asp | Asp | Phe | Asn | Gln | Leu | Tyr | Lys | Val | Tyr | Asn | Glu | Asp |
| | | | | 85 | | | | | 90 | | | | | 95 | |
| Lys | His | Leu | Cys | Ser | Trp | Trp | Asn | Gly | Phe | Leu | Phe | Pro | Leu | Val | Leu |
| | | | 100 | | | | | 105 | | | | | 110 | | |
| Lys | Thr | Ala | Asn | Asp | Ile | Ser | Ala | Tyr | Gly | Phe | Lys | Cys | Ala | Gly | Lys |
| | | 115 | | | | | 120 | | | | | 125 | | | |
| Gly | Ala | Thr | Lys | Gly | Tyr | Tyr | Glu | Val | Met | Gln | Asp | Asp | Val | Glu | Asn |
| | 130 | | | | | 135 | | | | | 140 | | | | |
| Ile | Ser | Asp | Asn | Gly | Tyr | Asp | Lys | Val | Ala | Gln | Glu | Lys | Ala | His | Lys |
| 145 | | | | | 150 | | | | | 155 | | | | | 160 |
| Asp | Leu | Gln | Ala | Arg | Cys | Lys | Ile | Leu | Ile | Lys | Glu | Ala | Asp | Gln | Tyr |
| | | | | 165 | | | | | 170 | | | | | 175 | |
| Lys | Ala | Ala | Ala | Asp | Asp | Val | Ser | Lys | His | Leu | Asn | Thr | Phe | Leu | Lys |
| | | | 180 | | | | | 185 | | | | | 190 | | |
| Gly | Gly | Gln | Asp | Ser | Asp | Gly | Asn | Asp | Val | Ile | Gly | Val | Glu | Ala | Val |
| | | 195 | | | | | 200 | | | | | 205 | | | |
| Gln | Val | Gln | Leu | Ala | Gln | Val | Lys | Asp | Asn | Leu | Asp | Gly | Leu | Tyr | Gly |
| | 210 | | | | | 215 | | | | | 220 | | | | |
| Asp | Lys | Ser | Pro | Arg | His | Glu | Glu | Leu | Leu | Lys | Lys | Val | Asp | Asp | Leu |
| 225 | | | | | 230 | | | | | 235 | | | | | 240 |
| Lys | Lys | Glu | Leu | Glu | Ala | Ala | Ile | Lys | Ala | Glu | Asn | Glu | Leu | Glu | Lys |
| | | | | 245 | | | | | 250 | | | | | 255 | |
| Lys | Val | Lys | Met | Ser | Phe | Ala | Leu | Gly | Pro | Leu | Leu | Gly | Phe | Val | Val |
| | | | 260 | | | | | 265 | | | | | 270 | | |
| Tyr | Glu | Ile | Leu | Glu | Leu | Thr | Ala | Val | Lys | Ser | Ile | His | Lys | Lys | Val |
| | | 275 | | | | | 280 | | | | | 285 | | | |
| Glu | Ala | Leu | Gln | Ala | Glu | Leu | Asp | Thr | Ala | Asn | Asp | Glu | Leu | Asp | Arg |
| | 290 | | | | | 295 | | | | | 300 | | | | |
| Asp | Val | Lys | Ile | Leu | Gly | Met | Met | Asn | Ser | Ile | Asp | Thr | Asp | Ile | Asp |
| 305 | | | | | 310 | | | | | 315 | | | | | 320 |
| Asn | Met | Leu | Glu | Gln | Gly | Glu | Gln | Ala | Leu | Val | Val | Phe | Arg | Lys | Ile |
| | | | | 325 | | | | | 330 | | | | | 335 | |
| Ala | Gly | Ile | Trp | Ser | Val | Ile | Ser | Leu | Asn | Ile | Gly | Asn | Leu | Arg | Glu |
| | | | 340 | | | | | 345 | | | | | 350 | | |
| Thr | Ser | Leu | Lys | Glu | Ile | Glu | Glu | Glu | Asn | Asp | Asp | Asp | Ala | Leu | Tyr |
| | | 355 | | | | | 360 | | | | | 365 | | | |
| Ile | Glu | Leu | Gly | Asp | Ala | Ala | Gly | Gln | Trp | Lys | Glu | Ile | Ala | Glu | Glu |
| | 370 | | | | | 375 | | | | | 380 | | | | |
| Ala | Gln | Ser | Phe | Val | Leu | Asn | Ala | Tyr | Thr | Pro | | | | | |
| 385 | | | | | 390 | | | | | 395 | | | | | |

( 2 ) INFORMATION FOR SEQ ID NO:7:

( i ) SEQUENCE CHARACTERISTICS:
( A ) LENGTH: 10 amino acids
( B ) TYPE: amino acid
( C ) STRANDEDNESS: single
( D ) TOPOLOGY: linear -continued ( i i ) MOLECULE TYPE: protein ( x i ) SEQUENCE DESCRIPTION: SEQ ID NO:7:

Ala Thr Leu Asn Glu Val Tyr Pro Val Asn
1 5 10

( 2 ) INFORMATION FOR SEQ ID NO:8:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:8:

Met Ile Ile Asp Ser Lys Thr Thr Leu Pro Arg His Ser Leu Ile Asn
1 5 10 15

Thr ( 2 ) INFORMATION FOR SEQ ID NO:9:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:9:

Gln Leu Gln Ala Gln Pro Leu Ile Pro Tyr Asn Val Leu Ala
1 5 10

( 2 ) INFORMATION FOR SEQ ID NO:10:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:10:

Met Ile Leu Gly Asn Gly Lys Thr Leu Pro Lys His Ile Arg Leu Ala
1 5 10 15

His Ile Phe Ala Thr Gln Asn Ser
20

( 2 ) INFORMATION FOR SEQ ID NO:11:

( i ) SEQUENCE CHARACTERISTICS:
( A ) LENGTH: 15 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:11:

Val Gln Arg Ile Leu Asp Glu Lys Leu Ser Phe Gln Leu Ile Lys
1 5 10 15

( 2 ) INFORMATION FOR SEQ ID NO:12:

( i ) SEQUENCE CHARACTERISTICS:
( A ) LENGTH: 21 bases

-continued ( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:12:

GCWACWTTAA ATGAAGTWTA T 21

( 2 ) INFORMATION FOR SEQ ID NO:13:

( i ) SEQUENCE CHARACTERISTICS:
( A ) LENGTH: 21 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:13:

AATGAAGTWT ATCCWGTWAA T 21

( 2 ) INFORMATION FOR SEQ ID NO:14:

( i ) SEQUENCE CHARACTERISTICS:
( A ) LENGTH: 38 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:14:

GCAAGCGGCC GCTTATGGAA TAAATTCAAT TYKRTCWA 38

( 2 ) INFORMATION FOR SEQ ID NO:15:

( i ) SEQUENCE CHARACTERISTICS:
( A ) LENGTH: 56 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:15:

ATGATTATTG ATTCTAAAAC AACATTACCA AGACATTCWT TAATWAATAC WATWAA 56

( 2 ) INFORMATION FOR SEQ ID NO:16:

( i ) SEQUENCE CHARACTERISTICS:
( A ) LENGTH: 38 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:16:

AAACATATTA GATTAGCACA TATTTTTGCA ACACAAAA 38

( 2 ) INFORMATION FOR SEQ ID NO:17:

( i ) SEQUENCE CHARACTERISTICS:
( A ) LENGTH: 17 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:17:

-continued

CAAYTACAAG C W CAACC 17

( 2 ) INFORMATION FOR SEQ ID NO:18:

( i ) SEQUENCE CHARACTERISTICS:
( A ) LENGTH: 21 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:18:

TTCATCTAAA ATTCTTTG W A C 21

I claim:

1. A process for controlling nematodes which comprises contacting said nematodes with a nematode-controlling effective mount of a toxin encoded by a *Bacillus thuringiensis* gene obtained from the nematicidally-active *Bacillus thuringiensis* isolate designated B.t-PS63B, said gone being found on a 4.4 kbp Xbal band by restriction fragment polymorphism analysis, and comprising an N-terminal amino acid of

QLQAQPLIPYNVLA; SEQ ID NO, 9, and comprising internal amino add sequence of

VQRILDBKLSFQLIK; SEQ ID NO. 11, said 4.4 kbp·XbaI band hydridizing under standard Southern blot conditions to an approximately 460 bp fragment which is generated by PCR using as primers SEQ ID NO. 17 and SEQ ID. 18; or a fragment thereof sufficient to encode a nematicidally-active toxin; wherein the nematode is selected from the group consisting of genera *Haemonchus, Trichostrongylus, Osrertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylogoma, Uncinaria, Toxascaris, Caenorhabditis, Parascaris, Bursaphalenchus, Criconenella, Ditylenchus, Globodera, Helicotylenchus, Heterodera, Meloidogyne, Pratylenchus, Radolpholus, Rotelynchus*, and *Tylenchus.*

2. A process for controlling nematodes which comprises containing said neroerodes with a nematode-controlling effective mount of a toxin encoded by a gene obtained from the nematicidally-active *Bacillus thuringiensis* isolate designated B.t PS63B, said gene found on a 4.4 kbp XbaI band by restriction fragment polymorphism analysis, and comprising an N-terminal amino add sequence of:

QLQAQPLIPYNVLA; SEQ ID NO. 9 and comprising an internal amino acid sequence of

VQRILDEKLSFQLIK; SEQ ID NO. 11, said 4,4 kbp XbaI band hybridizing under standard Southern blot conditions to approximately 460 bp fragment which is generated by PCR using as primers SEQ ID NO. 17 and SEQ ID NO. 18; or a fragment thereof sufficient to encode a nematicidally-active toxin.

* * * * *

UNITED STATES PATENT AND TRADEMARK OFFICE

CERTIFICATE OF CORRECTION

PATENT NO. : 5,439,881

DATED : August 8, 1995

INVENTOR(S) : Kenneth E. Narva, et al

It is certified that error appears in the above-indentified patent and that said Letters Patent is hereby corrected as shown below:

Column 1: lines 28-29: "et al. "The" should read --et al. [1980] "The--.

Column 2: line 50: "closing" should read --cloning--; line 51: "PS 33F 2toxin" should read --PS33F2 toxin--; line 54: "designed" should read --designated--.

Column 4: line 48: "off" should read --oil--.

Column 6: line 16: "and positive," should read --and -positive,--.

Column 8: line 34: "Natl. Atari." should read --Natl. Acad.--; line 40: omitted, should read --SEQ ID NO. 7--; line 41: omitted, should read --SEQ ID NO. 8--; line 42: omitted, should read --SEQ ID NO. 9--; line 43: omitted, should read --SEQ ID NO. 10--; line 49: "Kirsclmer" should read --Kirschner--; line 49: "Laemrnli" should read --Laemmli--; line54: omitted, should read --SEQ ID NO. 11--.

Column 9: line 34: "ethldium" should read --ethidium--; line 39: "32P-labelled" should read --$^{32}$P-labelled--; line 42: "5'GCA/F ACA/T TYA" should read --5' GCA/T ACA/T TTA--; line 43: omitted, should read --SEQ ID NO. 12--; line 45: omitted, should read --SEQ ID NO. 13--; line 53: "G A/G TC T/A A 3'" should read --C/T T/G A/G TC T/A A 3'--;

UNITED STATES PATENT AND TRADEMARK OFFICE
CERTIFICATE OF CORRECTION

PATENT NO. : 5,439,881 Page 2 of 4

DATED : August 8, 1995

INVENTOR(S) : Kenneth E. Narva, et al

It is certified that error appears in the above-indentified patent and that said Letters Patent is hereby corrected as shown below:

Column 9: line 53: omitted, should read --SEQ ID NO. 14--; line 62: "pHTBluell" should read --pHTBlueII--.

Column 10: lines 12-13: "acrystallfferous" should read --acrystalliferous--; line 64: "5' ATG ATY ATT" should read --5' ATG ATT ATT--; line 65: "TCA/T TYA ATA/T" should read --TCA/T TTA ATA/T--; line 66: omitted, should read --SEQ ID NO. 15--.

Column 11: line 36: "tom" should read --toxin--.

Column 12: line 17: "5' AAA CAT ATF AGA" should read --5' AAA CAT ATT AGA--; line 17: "CAT ATF TTF" should read --CAT ATT TTT--; line 18: omitted, should read --SEQ ID NO. 16--; line 68: omitted, should read --SEQ ID NO. 17--.

Column 13: lines 4-5: "TCT TTG AJTAC 3'" should read --TCT TTG A/TAC 3'--; line 5: omitted, should read --SEQ ID NO. 18--; line 13: "Hindl II" should read --HindIII--; line 21: "Leeroans," should read --Leemans,--; line 25: "Biofrechnology" should read --Bio/Technology--; lines 44-45: "Pennook, G.d.," should read --Pennock, G.d.,--.

UNITED STATES PATENT AND TRADEMARK OFFICE

CERTIFICATE OF CORRECTION

PATENT NO. : 5,439,881

DATED : August 8, 1995

INVENTOR(S) : Kenneth E. Narva, et al

It is certified that error appears in the above-indentified patent and that said Letters Patent is hereby corrected as shown below:

Column 14: line 10: "a Y-end" should read --a 3'-end--; line26: "Cor T" should read --C or T--; line 29: "QR=AG ff S" should read --QR = AG if S--; line 30: "J=AorG" should read --J = A or G--; line 31: "K=TorC" should read --K = T or C--; line 32: "L=A, T, CorG" should read --L = A, T, C or G--; line 33: "M=A, CorT" should read --M = A, C or T--; line 49: "pan" should read --part--.

Column 39: line 21: "mount" should read --amount--; line 24: "gone" should read --gene--; line 24: "Xbal" should read --XbaI--; line 26: "acid of" should read --acid sequence of--; line 27: "ID NO, 9," should read --ID NO. 9--; line 28: "amino add" should read --amino acid--; line 29: "VQRILDB" should read --VQRILDE--; line 30: "4.4. kbp·XbaI" should read --4.4 kbp XbaI--; line 33: "ID. 18" should read --ID NO. 18--; lines 36-37: "Osrertagia" should read --Ostertagia--.

Column 40: line 18: "Ancylogoma" should read --Ancylostoma--; lines 19-20: "Criconenella" should read --Criconemella--; line 24: "containing said neroerodes" should read --contacting said nematodes--;

UNITED STATES PATENT AND TRADEMARK OFFICE

CERTIFICATE OF CORRECTION

PATENT NO. : 5,439,881 Page 4 of 4

DATED : August 8, 1995

INVENTOR(S) : Kenneth E. Narva, et al

It is certified that error appears in the above-indentified patent and that said Letters Patent is hereby corrected as shown below:

Column 40: line 25: "mount" should read --amount--; line 27: "said gene found" should read --said gene being found--; line 30: "add sequence" should read --acid sequence--; line 34: "4,4 kbp" should read --4.4 kbp--; line 35: "to approximately" should read --to an approximately--.

Signed and Sealed this

Sixteenth Day of January, 1996

Attest:

BRUCE LEHMAN

Attesting Officer

Commissioner of Patents and Trademarks